United States Patent [19]
Zipes et al.

[11] Patent Number: 5,383,922
[45] Date of Patent: Jan. 24, 1995

[54] RF LEAD FIXATION AND IMPLANTABLE LEAD

[75] Inventors: Duglas P. Zipes, Carmel, Ind.; Clare P. Ulrich; Paul D. Blankenau, both of Minneapolis, Minn.; William M. Terrell, Coon Rapids, Minn.

[73] Assignee: Medtronic, Inc., Minneapolis, Minn.

[21] Appl. No.: 31,767

[22] Filed: Mar. 15, 1993

[51] Int. Cl.6 .............................................. A61N 1/04
[52] U.S. Cl. ...................................... 607/122; 607/101
[58] Field of Search ............... 607/119, 116, 122, 126, 607/101, 154

[56] References Cited

U.S. PATENT DOCUMENTS

| | | |
|---|---|---|
| 3,737,579 | 6/1973 | Bolduc . |
| 3,814,104 | 6/1974 | Irnich . |
| 3,844,292 | 10/1974 | Bolduc . |
| 3,902,501 | 9/1975 | Citron . |
| 3,937,225 | 2/1976 | Schramm . |
| 3,974,834 | 8/1976 | Kane . |
| 3,999,555 | 12/1976 | Person . |
| 4,149,542 | 4/1979 | Thoren . |
| 4,154,247 | 5/1979 | O'Neill . |
| 4,332,259 | 6/1982 | McCorkle, Jr. ............ 607/126 |
| 4,817,634 | 4/1989 | Holleman . |
| 4,945,912 | 8/1990 | Langberg ................... 607/101 |
| 5,044,374 | 9/1991 | Lindemans . |

Primary Examiner—Angela D. Sykes
Assistant Examiner—Scott M. Getzow
Attorney, Agent, or Firm—Reed A. Duthler; Harold R. Patton

[57] ABSTRACT

A method and apparatus for affixing implantable catheters and leads to body tissue. An electrode located on the lead or catheter is coupled to an RF signal generator, of the type employed to perform electrosurgical procedures such as electrocoagulation. The RF signal causes the electrode to adhere to body tissue, thus stabilizing the location of the catheter or lead. The electrode may be an electrode normally employed for other purposes, such as cardiac pacing, or may be a dedicated electrode employed only for affixation. Contact between the electrode and the RF signal generator may be made by a conductor permanently mounted within the catheter or lead, or by a removable conductor.

20 Claims, 6 Drawing Sheets

RF LEAD FIXATION AND IMPLANTABLE LEAD

BACKGROUND OF THE INVENTION

The present invention relates generally to medical electrical leads and more specifically to electrode leads used in conjunction with implantable pacemakers and implantable defibrillators.

Pacing and defibrillation leads are typically located on or in the human heart. The physician carefully places the leads so that their electrodes are located precisely in desired locations. However, the beating of the human heart tends to dislodge these leads from their desired locations. Therefore, over the years, a wide variety of methods and apparatus designed to retain the leads in their desired locations have been developed.

Lead fixation mechanisms can generally be divided into active fixation and passive fixation. Active fixation devices typically take the form of penetrating barbs, screws, or clamps which actively engage, and typically penetrate heart tissue as part of their retention function. Leads employing active fixation mechanisms include U.S. Pat. No. 3,737,579 issued to Bolduc, U.S. Pat. No. 3,814,104 issued to Irnich et al, U.S. Pat. No. 3,844,292 issued to Bolduc, U.S. Pat. No. 3,974,834 issued to Kane and U.S. Pat. No. 3,999,555 issued to Person. Passive fixation mechanisms are typically less severe, and tend to engage the heart tissue without penetrating it. Pliant tines, located upon the ends of the electrodes are the most commonly used passive fixation device. Such tines are disclosed in U.S. Pat. No. 3,902,501, issued to Citron, et al. Alternative passive fixation mechanisms include leads specifically shaped to brace against cardiac tissue, so that the electrodes will remain in a specific desired location, as well as fixation by means of tissue ingrowth, wedging, and so forth. Leads employing passive fixation mechanisms are also disclosed in U.S. Pat. No. 4,154,247 issued to O'Neill, U.S. Pat. No. 4,149,542 issued to Thoren and U.S. Pat. No. 3,937,225 issued to Schramm.

All of the fixation mechanisms described above have one or more drawbacks. Typically, passive fixation mechanisms are not as reliable in maintaining the leads in their desired locations as active fixation mechanisms, in the absence of trabeculation at the desired electrode location. Active fixation mechanisms typically require deployment of some sharpened member such as a screw or a barb, which adds substantial mechanical complexity, and in some cases risks unwanted perforation of heart tissue or snagging of the fixation devices on venous or valve tissue, during the implantation procedure. Thus, there is still a demand for improved fixation mechanisms, particularly those which do not significantly add to the mechanical complexity of the lead or to the difficulty of the implant procedure, but nonetheless provide reliable fixation at the time of implant.

SUMMARY OF THE INVENTION

The present invention is directed toward a new method of fixing of an implantable lead in place adjacent to body tissue. For purposes of this application, the term "lead" should be interpreted broadly as including any device of the types generally referred to as leads or catheters, so long as at least one electrode is included. While the invention can be employed in a number of different contexts, it is believed most likely to be used in the context of cardiac pacing and defibrillation electrode leads, for affixing the leads to desired locations on or in the heart or in the venous system adjacent the heart.

The present invention accomplishes these objects by means of coupling an electrode located on the lead body to an RF signal generator, of the type typically employed in conjunction with electrosurgical devices, such as electrocoagulators and the like. The lead is located at its desired implant site, and RF energy is applied to an electrode on the lead, causing the electrode to adhere to adjacent tissue. The inventors have determined that by applying RF energy levels typically used for electrocoagulation, for short periods of time (e.g., a few seconds) a reliable connection to the tissue can be made, with the strength of the connection being controlled by the duration of the RF signal. In this fashion, a light tack can be accomplished for temporary positioning, following which the lead may be relocated, and more permanent connection between the lead and the tissue made by meads of an RF signal of greater duration.

The electrode coupled to the RF generator may be a dedicated electrode located on the lead, specifically used only for fixation, may be one of the electrodes normally present on the lead, such as an indifferent electrode used for pacing and sensing, or may be a portion of a larger surface electrode such as a defibrillation electrode. The electrode may be connected to the RF source by means of an insulated stylet, which is passed through the lead body to couple electrodes to the RF generator, or by means of a conductor permanently mounted in the lead body.

After fixation, the RF source is disconnected and the lead is coupled to a medical device. If the lead carries an electrode which is coupled to an electrical connector, such as in electrical stimulation and monitoring leads, the lead and the electrode thereon will thereafter be coupled to an implantable pacemaker, defibrillator, or other implantable medical pulse generator or medical monitoring device. If the electrode on the lead is only used for fixation, the lead may be coupled to an implantable drug dispenser or other implantable device which employs a permanently implanted lead for therapeutic or monitoring purposes.

DETAILED DESCRIPTION OF THE PREFERRED EMBODIMENT

Figure 1:
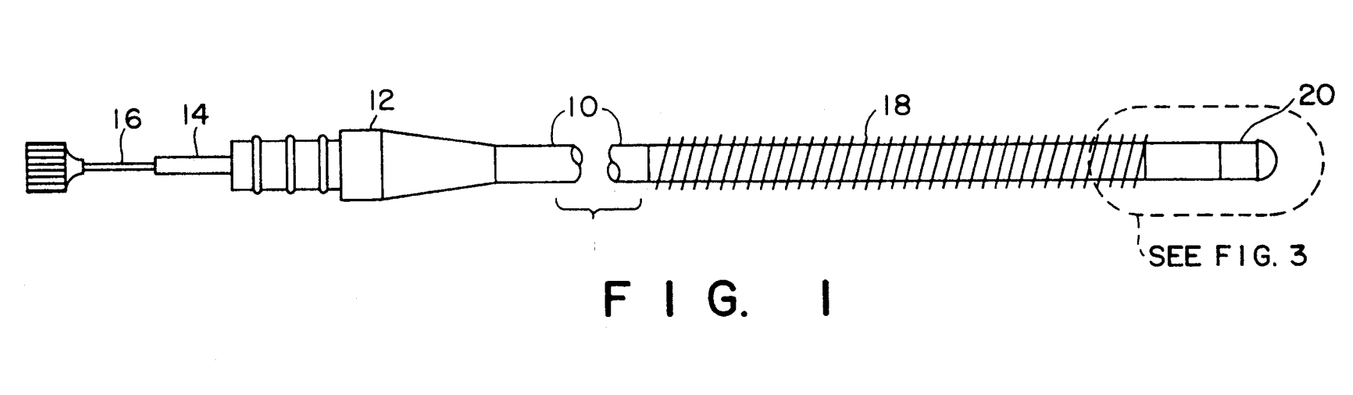
FIG. 1 is a plan view of a defibrillation lead employing the present invention.

FIG. 1 is a side plan view of a defibrillation lead, adapted for use in practicing the present invention. The lead is provided with an elongated insulative lead body 10, enclosing a coiled conductor which runs the length of the lead body. At the proximal end of the lead is a connector assembly 12, including a connector pin 14 coupled to the conductor within the lead body 10. A stylet 16 is shown inserted into connector pin 14. An elongated coil electrode 18 is located In the distal region of the lead, also coupled to the conductor within the lead body 10 and thereby to connector pin 14. This much of the structure of the illustrated lead is typical of prior art endocardial defibrillation leads.

Located adjacent to the distal end of the lead is a ring electrode 20, which is not coupled to the conductor within the lead body 10, but instead is coupled to an RF generator by means of stylet 16. Because electrode 20 is insulated from the connector assembly 12, it may not be employed for sensing or stimulation purposes. Although not visible in this illustration, stylet 16 is insulated over the majority of its length, being uninsulated only at its proximal and distal extremities, whereby the distal extremity of stylet 16 contacts electrode 20 internally to the lead and an alligator clip or other electrical connector may be coupled to the uninsulated proximal end of the stylet 16.

The general method of implantation of the lead of FIG. 1 comprises inserting the lead in its desired location (e.g., right ventricle, right atrium, superior vena cava or coronary sinus) and, when the lead is properly located, coupling an electrosurgical generator to stylet 16 and to a ground plate electrode mounted to the patient's body, which may be a return electrode of the type typically used in conjunction with the electrosurgical devices. RF energy is applied to the stylet and the return electrode, causing electrode 20 to become affixed to heart tissue. While the energy is employed to accomplish such fixation will vary from design to design, in general, fixation can be accomplished using a prior art RF electrosurgical power source within the range of power levels generally used for electrocoagulation. In addition, in devices so equipped, the impedance meter may be used to control the duration of application of the RF signal, with a change of impedance in the range of about 30% being useful to indicate that fixation has occurred.

Initial fixation or temporary fixation can be accomplished with an RF signal terminated prior to the occurrence of the above-mentioned impedance change, with permanent fixation being accomplished by extending the signal period until the change in measured impedance occurs. After fixation is accomplished, the stylet 16 is disconnected from the RF source and the stylet is removed from the lead. The lead is then coupled to an implantable defibrillator, with electrode 18 being coupled to the high voltage output of the defibrillator by means of connector pin 14.

Figure 2:
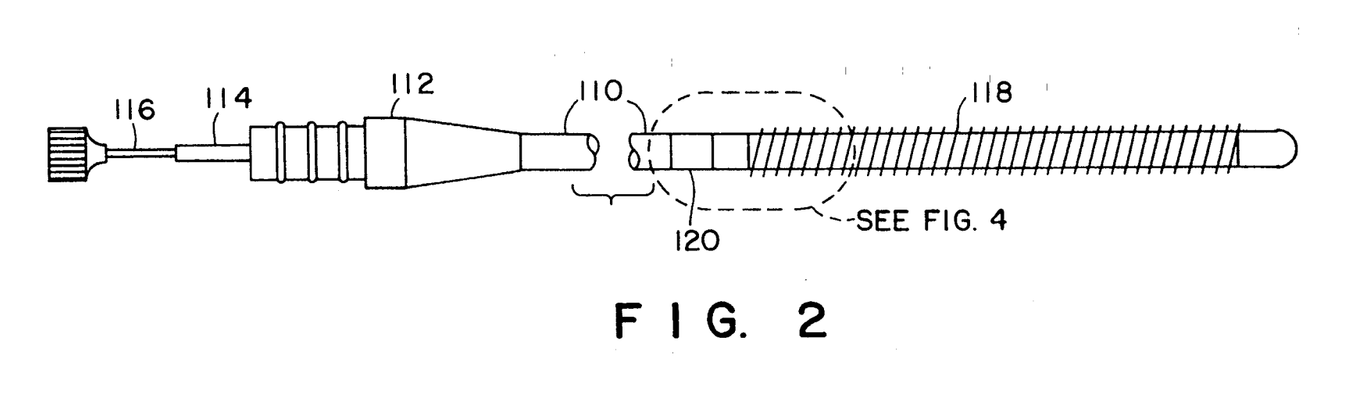
FIG. 2 is a plan view of a second embodiment of a defibrillation lead employing the present invention.

FIG. 2 discloses an alternate embodiment of the lead generally as illustrated in FIG. 1. Like the lead in FIG. 1, it includes an elongated insulative lead body 110 which carries a conductor coupled to coil electrode 118 and connector pin 114 which in turn is mounted to a connector assembly 112 on the proximal end of the lead. In this case, the fixation electrode 120 is located proximal to the coil electrode 118. Stylet 116 is an insulated stylet, corresponding to stylet 16 (FIG. 1), but coupled to electrode 120, as illustrated in more detail in FIG. 4.

Figure 3:
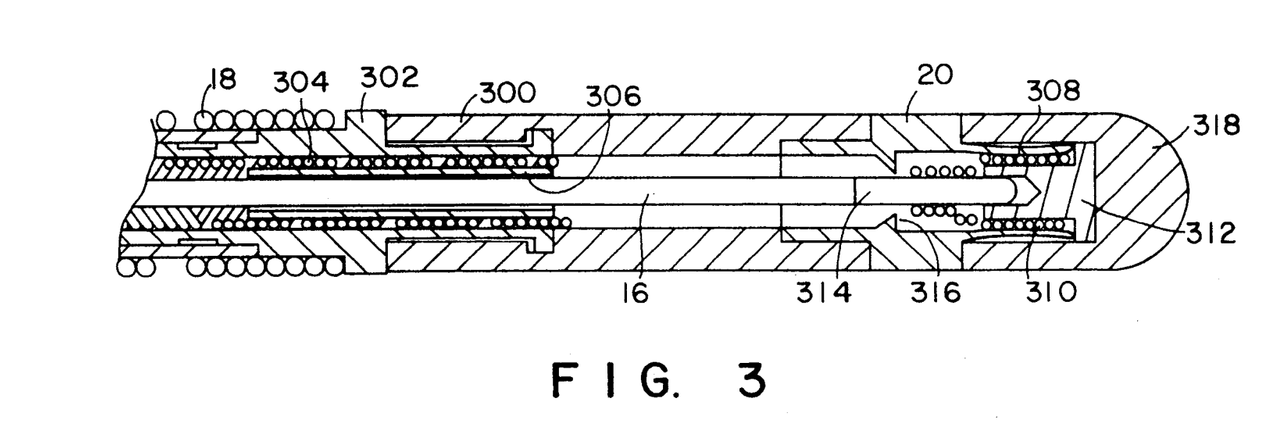
FIG. 3 is a cut away view through the distal tip of the lead illustrated in FIG. 1.

FIG. 3 is a sectional view through the distal end of the lead illustrated in FIG. 1. As illustrated, electrode 20 is located at the distal end of a sleeve 300 of a flexible insulative material, and is typically bonded adhesively thereto. The proximal end of sleeve 300 surrounds a crimp sleeve 302 to which electrode 18 is welded. The conductor 304 located within crimp sleeve 302 is coupled to the connector pin 14, illustrated in FIG. 1.

Crimping core 306 is provided internal to conductor 304, and conductor 304 is crimped between crimping sleeve 302 and crimping core 306 to couple it electrically and mechanically to electrode 18. Similarly, electrode 20 is provided with a cylindrical extension 308 which acts as a crimping sleeve. A crimping core 312 is provided, with coil 310 crimped between sleeve 308 and core 312. As illustrated, coil 310 serves as an electrical connector for coupling the uninsulated portion 314 of stylet 16 to electrode 20. The interior surface of ring electrode 20 is provided with a conical ramp 316, so that the distal 314 of stylet 16 is properly centered for entry into the proximal end of coil 310. The proximal end of coil 310 has an inner diameter slightly less than the outer diameter of the uninsulated portion 314 of stylet 16, to provide a low impedance electrical connection between stylet 16 and electrode 20. At the distal end of the lead, a rounded, insulative tip member 318 is provided.

Figure 4:
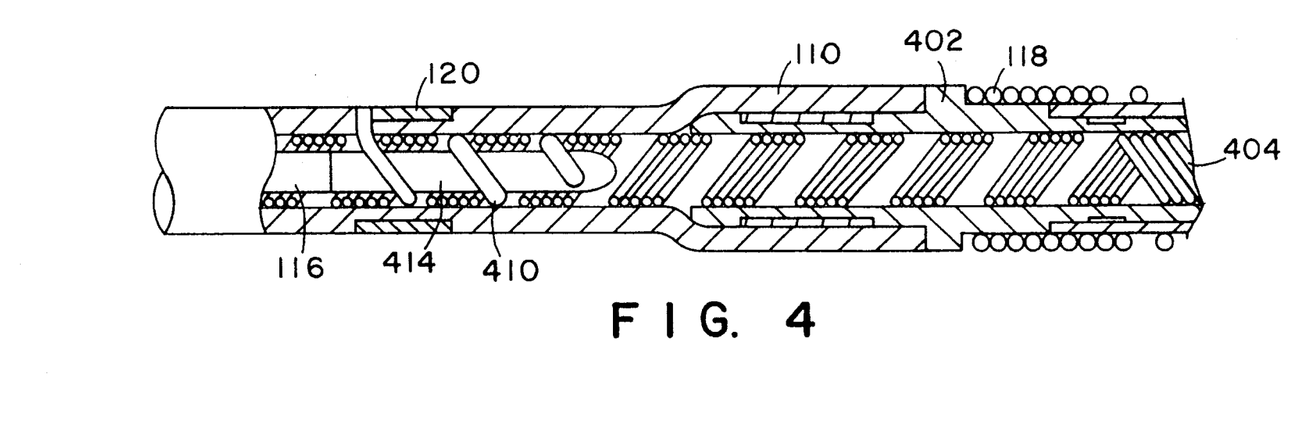
FIG. 4 is a cut away view of the lead illustrated in FIG. 2, adjacent the proximal end of the defibrillation electrode.

FIG. 4 is a cut away view through the area adjacent the proximal end of electrode 118 as illustrated in FIG. 2. The proximal end of coil electrode 118 is welded to a sleeve 402 which in turn is mounted adhesively to lead body 110. An elongated conductor 404 extends within lead body 110 and is coupled to connector pin 114 at the proximal end of the lead and to electrode 118 at the distal end thereof, by means of a crimp sleeve as illustrated in FIG. 3.

Ring electrode 120 is coupled to a coil 410 which is interwound in between the turns of multifilar coil 404, and insulated therefrom. Coil 410 may be insulated from coil 404 by means of an insulative coating applied to the conductors of coil 404 or by means of an insulative coating applied to all but the interior surface of coil 410. Coil 410 is shown engaging the uninsulated portion 414 of insulated stylet 116, coupling it electrically to electrode 120. The interior diameter of coil 410 is very slightly smaller than the outer diameter of stylet 414 providing a low impedance connection to electrode 120.

Figure 5:
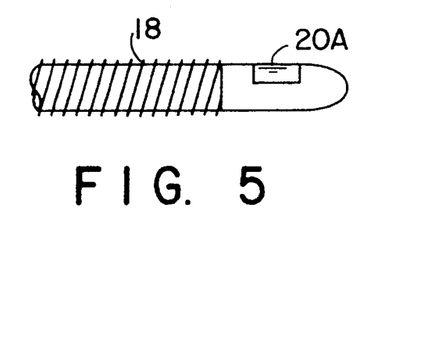
FIG. 5 is a plan view of the distal end of a first alternative embodiment of a lead generally as illustrated in FIG. 1.
Figure 6:
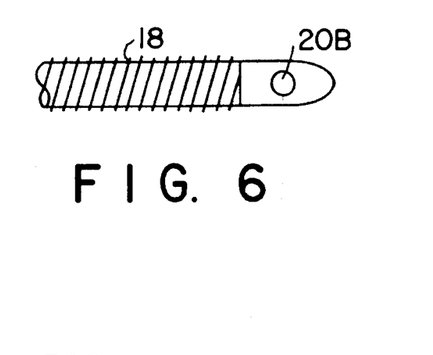
FIG. 6 is a plan view of the distal end of a second alternative embodiment of a lead generally is illustrated in FIG. 1.

FIG. 5 illustrates an alternative version of the distal end of the lead illustrated in FIG. 1. In this case, electrode 20A takes the form of a hemi-cylindrical electrode, rather than a complete cylindrical electrode as in FIG. 1. FIG. 6 correspondingly illustrates a button or point electrode 20B, as substituted for electrode 20 in FIG. 1. Electrodes 20A and 20B of FIGS. 5 and 6 are believed particularly valuable in the context of a coronary sinus lead where complete fixation around the entire circumference of the lead may not be desirable, particularly if the distal end of the lead is not intended to completely block the coronary sinus or great cardiac vein in which it is located. Similarly, point, button or other small surface area electrodes may be added to or substituted for electrodes presently existing cardiac pacing and defibrillation leads to provide the capability of fixing the lead body to heart tissue at whatever point is desired.

Figure 7:
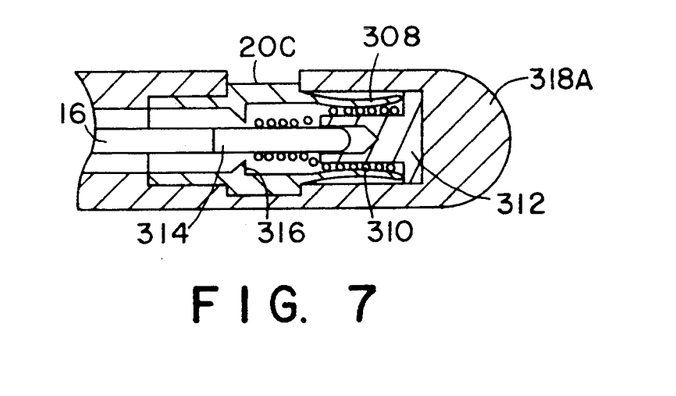
FIG. 7 is a cut away view through the distal end of the alternative embodiments illustrated in FIGS. 5 and 6, illustrating a recessed electrode configuration.
Figure 8:
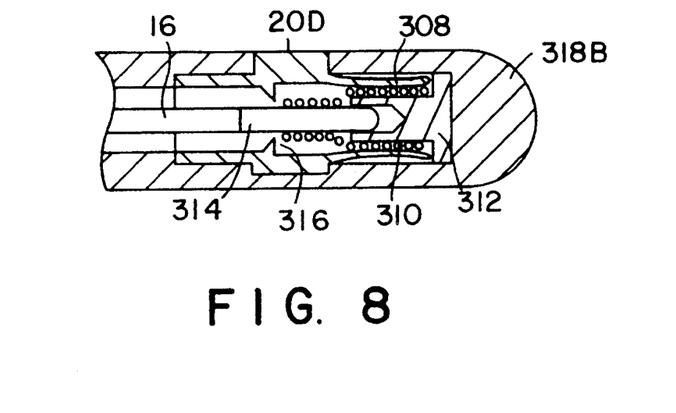
FIG. 8 is a cut away view through the distal end of the alternative embodiments illustrated in FIGS. 5 and 6, illustrating a flush mounted electrode configuration.

The electrodes 20A and 20B may be mounted flush to the surface of the lead or may be recessed. FIGS. 7 and 8 illustrate these two alternative electrode configurations. Numbered elements in FIG. 7 correspond to identically numbered elements in FIG. 3, with the exception that the insulative tip 318A of the lead extends back to the Crimp sleeve 302 (FIG. 3) and that the electrode 20C is recessed within the tip 318A and the exposed portion of the electrode, as in FIGS. 5 and 6, does not extend around the full circumference of the lead. FIG. 8 illustrates a lead in which the electrode 20D is mounted flush to the surface of tip 318B, but otherwise corresponds exactly to the lead illustrated in FIG. 7.

Figure 9:
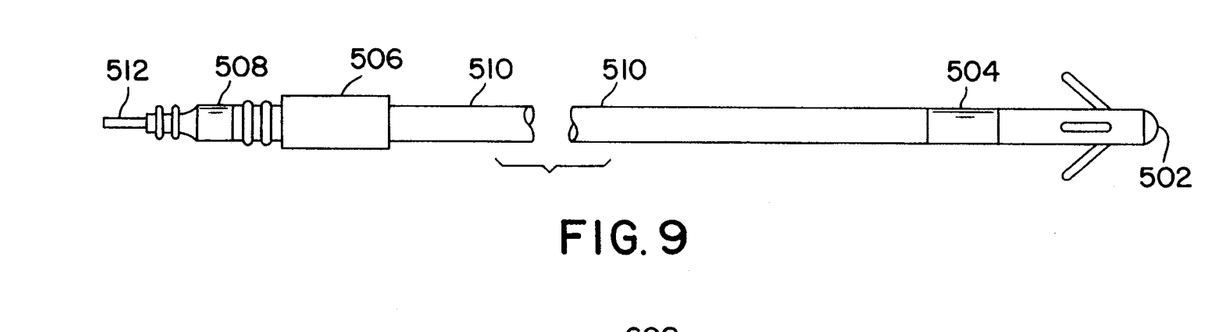
FIG. 9 is a plan view of a typical bi-polar pacing lead, which may be employed to practice the present invention.

FIG. 9 is an illustration of a prior art bi-polar tined pacing lead, of the type presently marketed by a number of manufacturers including Medtronic, Inc. Active pacing electrode 502 and indifferent ring electrode 504 are located adjacent the distal end of the lead. Connector assembly 506 carrying connector ring 508 and connector pin 512 are located at the proximal end of the lead. Connector pin 512 is coupled to tip electrode 502 and connector ring 508 is coupled to ring electrode 504 by means of coaxial, mutually insulated coiled conductors running the length of lead body 510.

In order for the lead of FIG. 9 to function properly, it is essential that electrode 502 be placed in an appropriate location in the heart, adjacent cardiac tissue which is preferably undamaged by either infarct, fibrosis or other causes, to allow for efficient pacing and sensing. However, it is not essential that ring electrode 504 be so located. Ring electrode 504 may be located adjacent heart tissue or it may float within the blood within either the atrium or the ventricle of the heart.

The inventors have determined that electrode 504 may be coupled to an electrosurgical power source by means of connector ring 508 and employed to provide a method of fixation of the lead of FIG. 5, in a fashion analogous to that provided by electrodes 20 and 120 in FIGS. 1 and 2, respectively.

After fixation is accomplished, the connector ring 514 is disconnected from the RF source and the lead is coupled to an implantable pacemaker, with electrode 502 coupled to the input and output stages of the pacer by means of connector pin 512. Electrode 504 may optionally be coupled to the pacer, or may be left uncoupled, such that the housing of the pacer provides an indifferent electrode for cardiac pacing.

Figure 10:
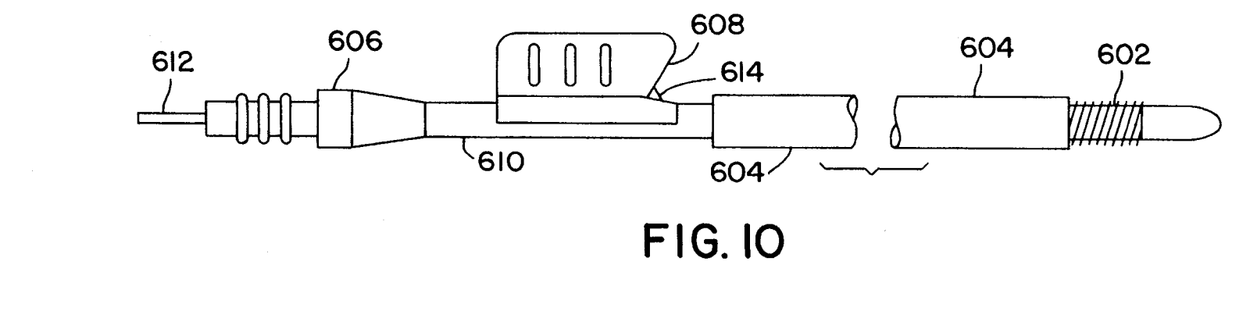
FIG. 10 is an illustration of a defibrillation lead, mounted in conjunction with an introducer set, facilitating use of only a portion of the electrode to fix the lead to heart tissue.

FIG. 10 illustrates a method of practicing the present invention using a prior art SVC/coronary sinus defibrillation lead. The lead is provided with an elongated insulative lead body 610, which carries a coil conductor therein coupling connector pin 612 on connector assembly 606 to an elongated coil electrode 602. In this method of practicing the present invention, the lead is inserted within an elongated sheath 604 of the type employed to introduce cardiac pacing leads, with the exception that sheath 604 extends from an area adjacent the proximal end of the lead all the way to the distal portion of electrode 602, covering all but the distal few turns of coil electrode 602. The lead is inserted into the coronary sinus or other desired location within sleeve 604, and then the RF generator is attached to pin 612 and a ground plate electrode, RF energy being applied to affix the proximal end of electrode 602 to affix it to adjacent heart tissue. After affixing the distal end of electrode 602 to heart tissue, the RF source is disconnected and the sleeve 604 is pulled in a proximal fashion over the blade 614 of a slitter 608, of the type presently manufactured by MedAmicus corporation in Minnetonka, Minn., and presently distributed by Medtronic, Inc. The blade 614 acts to split the sheath 604 so that it may be removed from the lead body 610. After removal of the sheath, 604 the slitter 608 is similarly removed from the lead body 610, allowing for the lead to then be coupled to an implantable defibrillator.

Figure 11:
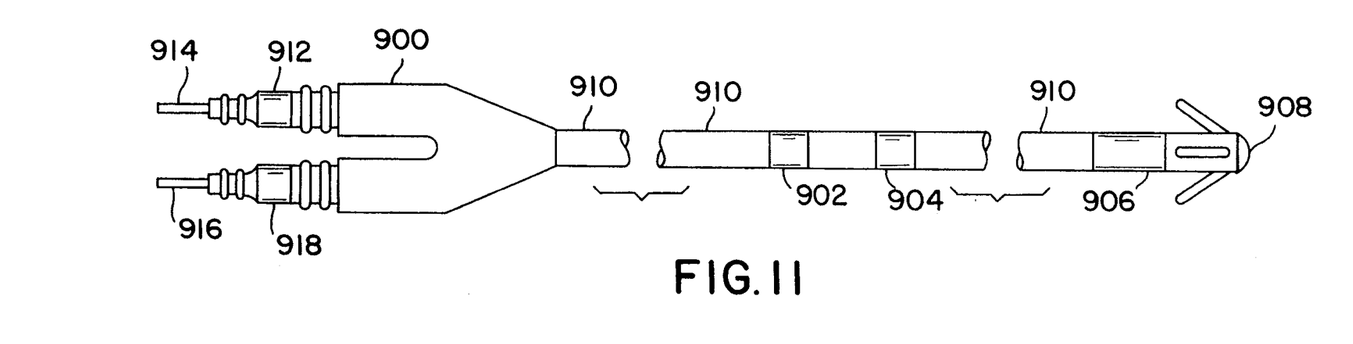
FIG. 11 is a plan view of a single pass A-V pacing lead, which may be employed to practice the present invention.

FIG. 11 is an illustration of a prior art single pass A-V pacing lead. Active ventricular pacing electrode 908 and indifferent ring electrode 906 are located adjacent the distal end of the lead. Atrial pacing electrodes 904 and 902 are located proximal to electrodes 906 and 908, spaced to allow their location in the atrium when electrodes 906 and 908 are properly located in the right ventricular apex. Connector assembly 900 carrying connector rings 912 and 918 and connector pins 914 and 916 is located at the proximal end of the lead. Connector pin 914 is coupled to tip electrode 908 and connector ring 912 is coupled to ring electrode 906 by means of mutually insulated coiled conductors running the length of lead body 910. Connector pin 916 is coupled to electrode 904 and connector ring 918 is coupled to ring electrode 902 by means of mutually insulated coiled conductors running the length of lead body 910.

In previous applications of the lead of FIG. 11, the atrial electrodes have generally been allowed to float within the right atrium, and have thus been employed primarily for sensing of atrial depolarizations, rather than for pacing the atrium. However, by employing one of the atrial electrodes 902 and 904 for fixation purposes, the other of the atrial electrodes may be employed to pace the atrium, in a manner analogous to the use of ventricular electrodes 504 and 508, as discussed above in conjunction with FIG. 9. In this fashion, the lead may be employed in conjunction with a DDD mode pacer, rather than being limited to use with VDD pacers.

Figure 12:
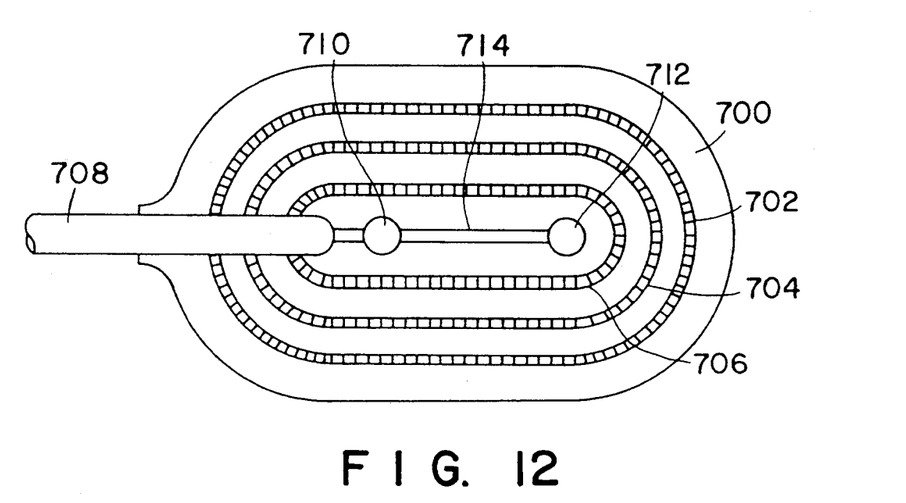
FIG. 12 is a plan view of the distal end of a subcutaneous or epicardial lead employing the present invention.

FIG. 12 illustrates an epicardial or subcutaneous lead employing the present invention. The lead corresponds generally to the leads disclosed in U.S. Pat. No 4,817,634 issued to Holleman et al and in U.S. Pat. No.

5,044,374, issued to Linderoans et al. The distal end of the lead is provided with a large surface area insulative electrode pad 700, carrying three concentric electrode coils 702, 704 and 706 coupled to an insulated conductor within lead body 708.

Two electrodes 710 and 712 are provided for fixation purposes, coupled to insulated conductor 714. Conductor 714 may extend to the proximal end of the lead to an electrical connector located thereon or may terminate in the vicinity of the pad 700, with electrical connection to conductor 714 and to electrodes 712 and 710 being made by means of an uninsulated stylet as in the leads of FIGS. 1 and 2. In either case, RF energy applied to electrodes 710 and 712 may be used to affix the electrode pad to tissue in a desired epicardial or subcutaneous location, for use in an implantable defibrillation lead system, in the same manner as described above in conjunction with FIGS. 1, 2 and 6.

Figure 13:
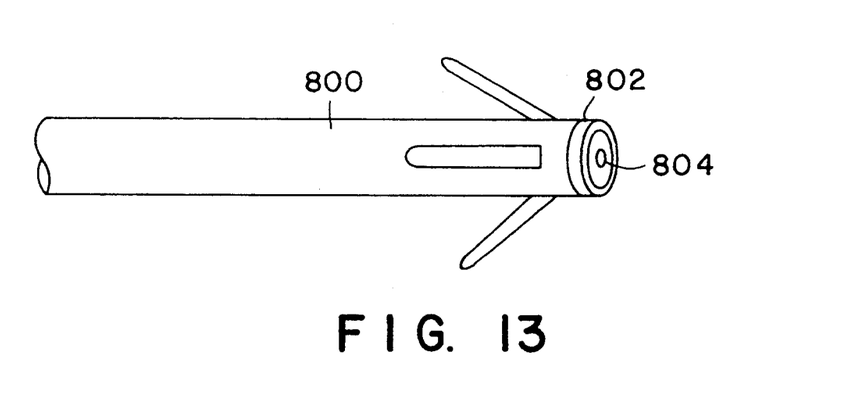
FIG. 13 is a plan view of the distal end of an endocardial lead employing the present invention.

FIG. 13 illustrates the distal end of yet another embodiment of an endocardial lead employing the present invention. In this case, the pacing and sensing electrode 802 takes the form of a ring shaped electrode mounted at the distal tip of lead body 800 and is connected to an insulated conductor mounted within lead body 800. A fixation electrode 804 is provided, located centrally within ring electrode 802 and insulated therefrom. As in the leads illustrated above, electrical connection to electrode 804 may be made by an insulated stylet or by a conductor permanently mounted in lead body 800, with fixation and connection to an implantable pacemaker otherwise corresponding to the description of FIG. 5, above.

Figure 14:
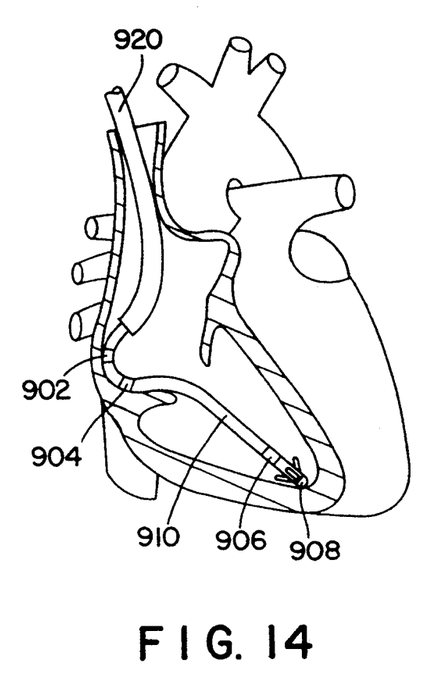
FIG. 14 is a cut away view of a human heart illustrating the location of a pacing lead as illustrated in FIG. 11 in the atrium and ventricle of a human heart.

FIGS. 14 illustrates the location of a leads as illustrated in FIG. 11 in the right ventricle and right atrium of the heart. In the context of the present invention, the lead is passed into the ventricle through a guide catheter 920. After finding an appropriate location for electrode 908 in the ventricle, guide catheter 920 is employed to located electrodes 902 and 904 at an appropriate position in the atrium. Depending on which of electrodes 902 and 904 is intended to be used for fixation, an electrosurgical generator is coupled to connector ring 918 or connector pin 916 and to a ground plate electrode, as described above in conjunction with the leads in FIG. 1 and 2 in order to affix the selected atrial electrode to heart tissue. While this will cause some damage to the tissue adjacent the selected electrode, it should not interfere with its function as an indifferent electrode, allowing pacing and sensing using the other atrial electrode. Alternatively, the lead could be connected as a unipolar lead for purposes of atrial pacing and sensing, with one of the atrial electrodes used only for permanently fixing the lead to heart tissue, and the other for pacing and sensing.

Figure 15:
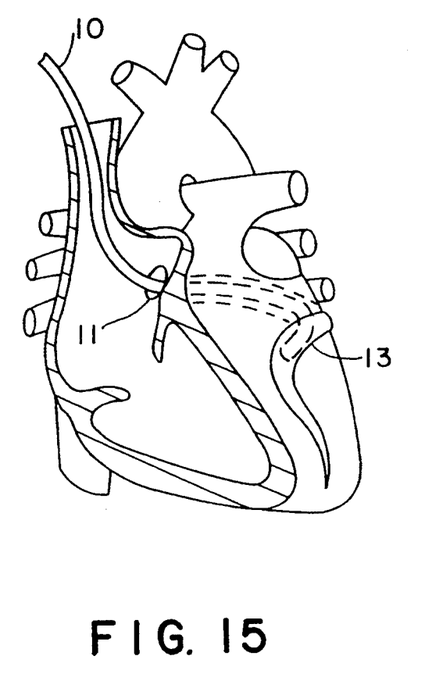
FIG. 15 is a cut away view of a human heart illustrating the location of a defibrillation lead as in FIG. 1, in the coronary sinus.

FIG. 15 illustrates the location of a lead as illustrated in FIG. 1 and 2, as located in the coronary sinus. In the context of the present invention, after finding an appropriate location for electrode 20 or 120 in the great cardiac vein or coronary sinus, an electrosurgical generator may be coupled to stylet 16 or 116 and to a ground plate electrode, as described above in order to affix electrode 20 or 120 to heart tissue. The lead of FIG. 6 may be similarly located, with the distal end of electrode 602 used to affix the lead to the wall of the great cardiac vein.

Figure 16:
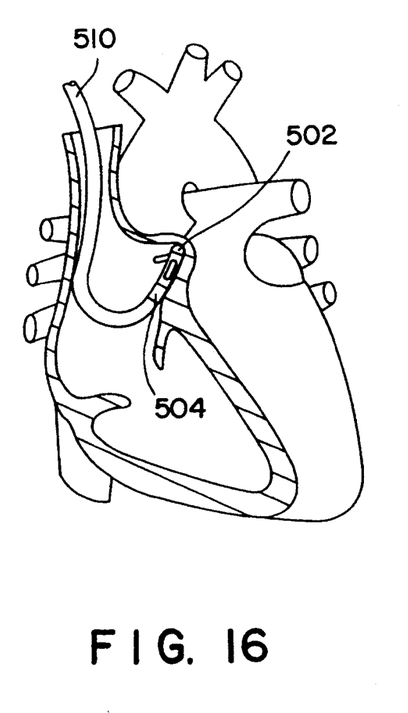
FIG. 16 is a cut away view of a human heart illustrating the location of a pacing lead as illustrated in FIG. 5 in the atrium of a human heart.
Figure 17:
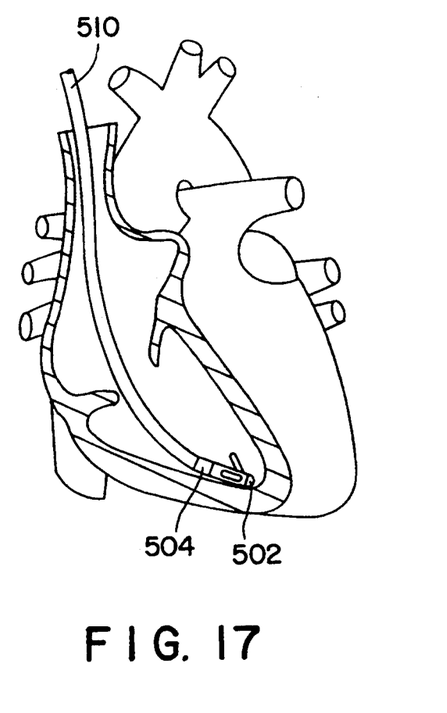
FIG. 17 is a cut away view of the human heart illustrating the location of a pacing lead as illustrated in FIG. 5, in the right ventricle.

FIGS. 16 and 17 illustrate the location of leads as illustrated in FIG. 9 in the right ventricle and right atrium of the heart, respectively. In the context of the present invention, after finding an appropriate location for electrode 502 in the atrium or the ventricle, an electrosurgical generator may be coupled to connector ring 508 and to a ground plate electrode, in order to affix electrode 504 to heart tissue. While this will cause some damage to the tissue adjacent ring electrode 504, it should not interfere with this function as an indifferent electrode, allowing continued pacing and sensing. Alternatively, the lead illustrated in FIG. 9, could be connected as a unipolar lead for purposes of pacing and sensing, with electrode 504 used only for permanently fixing the lead to heart tissue.

As such, the present invention provides a new mechanism for fixing cardiac pacing leads and defibrillation leads to body tissue, by means of application of an RF signal to an electrode located on the lead. The electrode may be a dedicated electrode used solely for fixation purposes or may be an electrode which is also used for sensing or stimulation purposes, as illustrated in FIGS. 5 and 6. The electrode may take any of a number of different forms, as illustrated in FIGS. 1-13, and may be coupled to a conductor located within the lead, or may be coupled to an RF generator by means of an insulated stylet or other temporary conductor placed in the lead body, solely during the fixation process. The present invention may be employed to locate leads in the coronary sinus, atrium, ventricle or other location within the cardiovascular system or subcutaneously.

While not specifically illustrated in the drawings, the present invention is also applicable to electrode leads located in other portions of the human body, such as nerve or muscle stimulation electrodes. Similarly, the invention may also be practiced in leads that do not employ stimulating electrodes, such as used for localized delivery of drugs in conjunction with implantable drug dispensers. In this context, the invention would be realized by adding an electrode to the drug delivery tube, and employing a conductor or an insulated stylet to deliver RF energy to the electrode in the fashion discussed above in conjunction with the illustrated embodiments. As such, the embodiments illustrated above should be taken as exemplary, rather than limiting, with regard to the scope of the claims which follow:

We claim:

1. A method of affixing a medical lead having an electrode at a desired location within a patient's body, comprising:
    positioning said electrode adjacent body tissue at said desired location and coupling said electrode to a source of RF electrical energy;
    applying RF electrical energy to said electrode to affix said electrode to said tissue; and
    disconnecting said source of RF energy from said electrode and allowing said lead to remain affixed to said tissue.

2. A method according to claim 1 wherein said positioning step comprises positioning said electrode adjacent heart tissue.

3. A method according to claim 2 wherein said positioning step comprises positioning said electrode in the ventricle.

4. A method according to claim 2 wherein said positioning step comprises positioning sad electrode in the atrium.

5. A method according to claim 2 where n said positioning step comprises positioning said electrode in the coronary sinus.

6. A method according to claim 2 wherein said positioning step comprises positioning said electrode in the superior vena cava.

7. A method according to claim 2 wherein said positioning step comprises positioning sad electrode on the epicardium.

8. A method according to claim 1 where n said positioning step comprises positioning said electrode subcutaneously.

9. A method according to claim 1 further comprising the step of coupling said lead to an implacable medical device after said disconnecting step.

10. A method according to claim 1 further comprising the step of coupling said electrode to an implantable medical device after said disconnecting step.

11. A method according to claim 1 further comprising the step of coupling said electrode to an implantable pulse generator after said disconnecting step.

12. A method according to claim 1 further comprising the steps of:
covering a portion of said electrode with an insulative material prior to said step of applying said RF electrical energy; and
removing said insulative material following said step of applying said RF electrical energy.

13. A medical lead comprising:
an elongated lead body;
a first electrode, mounted to said lead body;
a conductive stylet, removably insertable in said lead body; and
means within said lead body for electrically coupling said stylet to said first electrode, said first electrode and said coupling means electrically isolated from all components of said lead except for said conductive stylet.

14. A medical lead comprising:
an elongated lead body;
a first electrode, mounted to said lead body;
a conductive stylet, comprising electrical insulation covering said stylet along its length, with a portion of said stylet not covered by said insulation, said stylet removably insertable in said lead body; and
means within said lead body for electrically coupling said portion of said stylet not covered by insulation to said first electrode.

15. A lead according to claim 13 or claim 14, further comprising:
a second electrode, mounted to said lead body;
an elongated conductor, within said lead body, electrically coupled to said second electrode; and
an electrical connector, mounted to said lead body and electrically coupled to said conductor.

16. A lead according to claim 14, further comprising connector means for coupling said lead to an implantable medical device, and wherein said first electrode is electrically isolated from said coupling means.

17. A medical lead comprising:
an elongated lead body;
a first electrode, mounted to said lead body;
a conductive stylet, removably insertable in said lead body; and
means within said lead body for electrically coupling said stylet to said first electrode
one or more electrical conductors permanently mounted within and extending through said lead body; and
electrical conductors for electrically coupling to said conductor means, mounted to said lead body; and
wherein said first electrode is electrically isolated from all said permanently mounted conductors within said lead body.

18. A lead according to claim 13 or claim 17 wherein said stylet comprises electrical insulation covering said stylet along its length, with a portion of said stylet not covered by said insulation, where by said portion not covered may be electrically coupled to said first electrode.

19. A lead according to claim 13 or claim 14 or claim 17, wherein said first electrode is recessed within said lead body.

20. A lead according to claim 13 or claim 14 or claim 17, wherein said first electrode extends circumferentially around one half or less of said lead body.

* * * * *

UNITED STATES PATENT AND TRADEMARK OFFICE
CERTIFICATE OF CORRECTION

Page 1 of 2

PATENT NO. : 5,383,922
DATED : JANUARY 24, 1995
INVENTOR(S) : Zipes et al.

It is certified that error appears in the above-indentified patent and that said Letters Patent is hereby corrected as shown below:

Title page, item [75]
Inventor: delete "Duglas P. Zipes", and insert in its place --Douglas P. Zipes--.

Inventor: delete "William M. Terrell", and insert in its place --Terrell M. Williams--.

Column 10, line 25, delete" conductors" and insert in its place --connector means--.

Column 10, line 26, delete "conductor means", and insert in its place --conductors--.

Column 7, line 1, delete "Linderoans", and insert in its place --Lindemans--.

Column 8, line 64, delete "sad", and insert in its place --said--.

Column 8, line 66, delete "where n", and insert in its place --wherein--.

Column 9, line 5, delete "sad", and insert in its place --said--.

Column 9, line 7, delete "where n", and insert in its place --wherein--.

UNITED STATES PATENT AND TRADEMARK OFFICE
CERTIFICATE OF CORRECTION

PATENT NO. : 5,383,922
DATED : January 24, 1995
INVENTOR(S) : Zipes, et. al.

It is certified that error appears in the above-indentified patent and that said Letters Patent is hereby corrected as shown below:

Column 9, line 11, delete "implacable", and insert in its place--implantable--.

Signed and Sealed this

Twenty-sixth Day of September, 1995

Attest:

BRUCE LEHMAN

*Attesting Officer*   *Commissioner of Patents and Trademarks*